United States Patent
Shaw

[11] Patent Number: 5,997,512
[45] Date of Patent: Dec. 7, 1999

[54] RETRACTABLE DENTAL SYRINGE

[76] Inventor: Thomas J. Shaw, 1510 Hillcrest, Little Elm, Tex. 75068

[21] Appl. No.: 09/034,411

[22] Filed: Mar. 4, 1998

[51] Int. Cl.[6] ...................................................... A61M 5/32
[52] U.S. Cl. ............................................ 604/195; 604/232
[58] Field of Search ..................................... 604/110, 187, 604/195, 198, 263, 232

[56] References Cited

U.S. PATENT DOCUMENTS

| | | | |
|---|---|---|---|
| 3,306,290 | 2/1967 | Weltman | 128/218 |
| 4,820,275 | 4/1989 | Haber et al. | 604/198 |
| 4,927,414 | 5/1990 | Kulli | 604/110 |
| 5,019,044 | 5/1991 | Tsao | 604/110 |
| 5,084,018 | 1/1992 | Tsao | 604/110 |
| 5,188,599 | 2/1993 | Botich et al. | 604/110 |
| 5,330,430 | 7/1994 | Sullivan | 604/134 |
| 5,330,440 | 7/1994 | Stanners et al. | 604/195 |
| 5,385,551 | 1/1995 | Shaw | 604/110 |
| 5,423,758 | 6/1995 | Shaw | 604/110 |
| 5,613,952 | 3/1997 | Pressly, Sr. et al. | 604/110 |
| 5,632,733 | 5/1997 | Shaw | 604/195 |
| 5,634,909 | 6/1997 | Schmitz | 604/232 X |
| 5,681,292 | 10/1997 | Tober et al. | 604/195 |
| 5,800,403 | 9/1998 | Pressly, Sr. et al. | 604/195 |
| 5,891,104 | 4/1999 | Shonfeld et al. | 604/232 X |

Primary Examiner—John D. Yasko
Attorney, Agent, or Firm—Locke Liddell & Sapp, LLP

[57] ABSTRACT

A single use retractable medical device dispenses fluids from a separable carpule. A retraction mechanism having a spring loaded needle holder with a double ended needle is mounted the in front of a housing by means of a push ring slidingly mounted on a widened portion of the needle holder. An outer edge of the push ring grips or is restrained by the inner wall surface of the housing to hold the needle holder in place. A carpule positioned through an opening in back of the housing is progressively received by a plunger which drives a separable two-part piston to unload medicine from the carpule through the needle. At the end of an injection, the plunger is depressed further to remove the push ring in cooperation with the carpule thereby freeing the needle holder for retraction through the front opening of the carpule. As the needle is retracted into the housing from one end, the edge of the thumb cap of the plunger disappears into an opening at the opposite end of the housing. An alternative embodiment has a thumb ring instead of a thumb cap. The alternate version has a dish shaped push ring with forwardly angled edges which tend to bind against the housing when pushed from the center by the front of the carpule. The edge of the push ring is easily released by an outer wall portion of the plunger which unlocks the dished edges from a stop structure on the inner wall of the housing as the plunger is moved forward to retract after an injection is made.

39 Claims, 5 Drawing Sheets

RETRACTABLE DENTAL SYRINGE

FIELD OF THE INVENTION

The present invention is a retractable medical device, more particularly, a retractable device that employs a removable medicine container.

BACKGROUND OF THE PRIOR ART

Conventional syringes have a barrel and a closely fitting piston which draws fluid into the barrel via a needle in front of the barrel. Fluid is drawn into the barrel through the needle, the air is expelled and an injection is made by depressing the plunger. Many of these medical devices have been designed to retract the needle by various mechanisms because of the continuing danger of exposed needles contaminated with infectious agents. With the increase of dangerous communicable diseases such as AIDS, it has become critical to eliminate needle stick injuries to medical personnel. Intensive efforts have been directed to development of retractable syringes which are safe, effective and practical, which can be mass produced at low cost.

Seemingly ignored in all this activity is the smaller but still significant group of syringes which employ a pre-filled cartridge of fluid medication and a double ended hypodermic needle communicating with the cartridge for injecting the contents of the cartridge. The pre-filled syringe cartridges are referred to as "carpules". They are typically cylindrical tubes with a puncturable membrane in front and a piston seal at the rear which is pressed forward by some form of plunger. The most common of these are the carpule syringes used by dentists in freezing the gums of their patients prior to their performing dental work on their teeth. Typically, the syringe enclosures with which such pre-filled syringe cartridges are used are not easily capable of retracting the needle into a protective enclosure to avoid inadvertent and potentially harmful needle sticks. Consequently, most syringes used for this purpose by dentists have a fixed needle which must be sheathed.

The relatively few attempts that have been made to produce a retractable needle syringe have produced results not altogether satisfactory. Weltmnan, U. S. Pat. No. 3,306, 290; Sullivan, U. S. Pat. No. 5,330,430; and Haber, U.S. Pat. No. 4,820,275 among other things suffer from the deficiency that the device is necessarily much longer than the stroke the plunger itself would require in order that the outer shell house both needle and cartridge. Stanners, U. S. Pat. No. 5,330,440, although it doesn't suffer from the length deficiency, employs special thread engaging plugs in both ends of the carpule and plunger. These threaded connections must be mechanically connected together to withdraw the needle to the back of th e special carpule. Retraction is done manually by disengaging a catch.

Although the needles can be retracted, these devices do not provide instantaneous retraction of the needle automatically at the end of an injection by further depression of the plunger while the needle is still in the patient's tissue. A slow controlled manual retraction of the needle is undesirable. Unintended movement of the syringe could damage tissue. Carpule syringe devices that would meet the above objections and which enable instantaneous retraction by continuation of the same motion used for the injection would be a significant improvement. These and other objects are the subject of the present invention.

SUMMARY OF THE INVENTION

The present invention is a single use retractable medical device which employs a modified carpule having a two-part sliding piston seal in back and a sliding seal in front. The retractable medical device is especially well suited for use as a dental syringe and one embodiment employs a thumb ring at the back of the plunger as is typical with dental syringes. The syringe is designed to retract after the injection by the simple expedient of continued depression of the plunger without moving the syringe away from the patient. The retraction parts and most of the needle are retracted into the carpule. All of the needle is retracted into the housing instantaneously upon depression of the plunger after the injection.

The carpule is unconventional mainly in the closures at the front and back end. The carpule has a cylindrical wall defining a fluid chamber and a front end with an opening into the fluid chamber and an open back end. A slidable front seal is lodged in the opening of the front end. The conventional carpule has no need for a sliding seal to cover the opening of the front end which is punctured by a rearwardly extending needle when the carpule is inserted. The modified carpule has a two-part sliding piston seal lodged in the open back end. The piston seal comprises an outer rim portion in sliding sealed contact with the wall of the fluid chamber and a slidably removable core portion. The sliding piston seal is moved by a plunger to the front of the fluid chamber to dispense all fluid. When driven in a retraction direction, the sliding front seal removes the core of the piston seal and traverses through the rim portion to enter the chamber along with following portions of a retraction mechanism.

The retractable medical device has a tubular housing having a wall defining a front end portion, a main body portion, an open back end and an inner surface defining a hollow interior. A retraction mechanism is mounted in the front end portion of the housing. The retraction mechanism comprises a needle holder having an elongated body with a front, a back and a widened part of the body spaced behind the front. Needle portions extend from the front and back of the needle holder. A spring is mounted under the widened part of the needle holder to apply retraction force thereto.

A releasable push ring is grippingly mounted around the widened part of the needle holder along a longitudinal interface. The push ring extends radially outwardly to the inner wall of the housing. Outer edges of the push ring are preferably in sliding gripping contact with the housing to hold the needle holder in place against the retraction force provided by the spring. The housing wall may be provided with stops behind the push ring to prevent rearward motion of the push ring and retraction mechanism.

A carpule of the type described above is inserted into the housing with the front seal in contact with the back end of the needle holder and punctured by the needle. The front of the carpule faces the push ring. A plunger is adapted to progressively receive the carpule while entering the housing and pressing the slidable piston forward to dispense fluid through the needle.

The plunger has a wall part that presses the outer rim part of the piston seal so that the core portion can slide rearwardly relative to the rim portion during retraction without being obstructed by the plunger. The plunger also has another wall part which presses against the outer edge portions of the push ring when the piston seal is fully depressed to the front of the carpule at the end of an injection. Retraction occurs by further depression of the plunger to move the push ring from the widened part of the needle holder while dislodging the front seal and the separable core part of the piston seal. Forward movement of the carpule against the needle holder frees the front seal and core part of the rear piston seal so that retraction force drives the needle holder and needle through the front opening into the carpule where they are safe. The carpule and the push ring are moved into a necked end part at the front of the housing simultaneously allowing a thumb cap to enter the back of the housing where the edge cannot be reached. It may be said to "disappear" within the housing. In an alternate version of the plunger, a traditional thumb ring is used in place of the thumb cap. Although the thumb ring allows withdrawal of the plunger after retraction, the parts cannot be reassembled for reuse because there is virtually no way to retrieve the outer rim portion of the piston which is lodged next to the wall just behind the front opening.

An alternate structure which may be used with either form of plunger, comprises a dish shaped push ring having a center body portion with a forwardly angled outer rim portion in contact with the wall of the housing and an opening with interfacing surfaces which slidingly grips the widened part of the needle holder. The housing has a small stop structure positioned under the push ring to provide overcomable resistance to movement thereof. The alternate version of the push ring tends to jam or bind the outer rim or edge against the wall of the housing because of a slight degree of flexing purposefully provided wherein the center moves forward slightly with respect to the edges which are held by the stop structure. This tends to prevent force imposed by the carpule by depression of the plunger during an injection from prematurely releasing the push ring from the needle holder. At the "end of injection" position, the plunger has an outer wall which lies along the wall of the housing pressing against the outer edge portion of the push ring. Forward movement of the plunger releases the edge of the push ring from the locking surfaces so that the push ring may be removed easily. The angled outer rim portion may have angled segments which help interact with the stop structure on the inner wall surface of the housing to hold the push ring in place until it is released by the plunger.

The parts are relatively uncomplicated and subject to mass production and automated assembly. The push ring may be assembled with the unneedled needle holder in an upright position, the spring placed on the needle holder and the housing dropped over the assembled parts to compress the spring as the push ring and needle holder is moved forward. The needle can be inserted from the front. This is the first practical retractable dental carpule syringe which retracts by continuation of the same motion used for injection and which retracts the needle directly from tissue to eliminate risk of needle stick with a contaminated needle. It uniquely employs the used carpule to receive the contaminated needle.

DETAILED DESCRIPTION OF THE INVENTION

Figures 2, 2A, 2B:
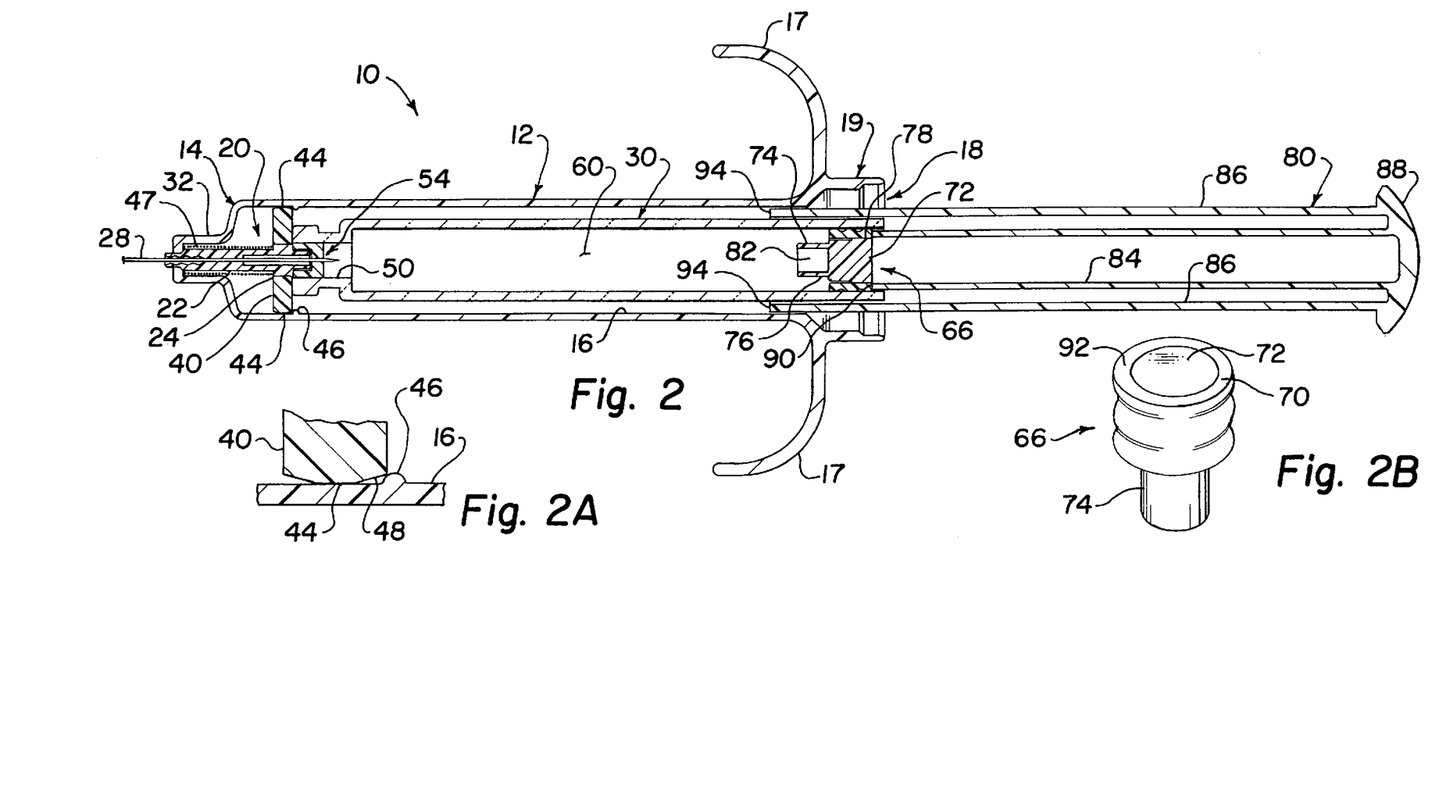
FIG. 2 is a cross section through the retractable medical device with the retraction mechanism mounted in front of the housing and the front of the carpule positioned behind the push ring with the front seal punctured by the double-ended needle.
FIG. 2A is an enlarged area of the outer edge of the push ring and wall of the housing showing an annular ring which slightly reduces the inside diameter to help hold the push ring and needle holding assembly from moving in the direction of retraction.
FIG. 2B is a perspective view of the two part sliding piston seal which is lodged in the back opening of the carpule seen in cross section in FIG. 2.

In the description that follows the same parts will be referred to with the same reference numerals and like parts may be indicated by applying a prime mark (') to reference numerals. A retractable medical device 10 is shown in FIG. 2 in the ready to use position. Tubular housing 12 has a front portion 14, an inner wall surface 16, and an open back end 18. Open back end 18 has a widened portion 19 to receive the thumb cap 88 on the back of a plunger 80 having a pair of finger grips 17.

Figure 3:
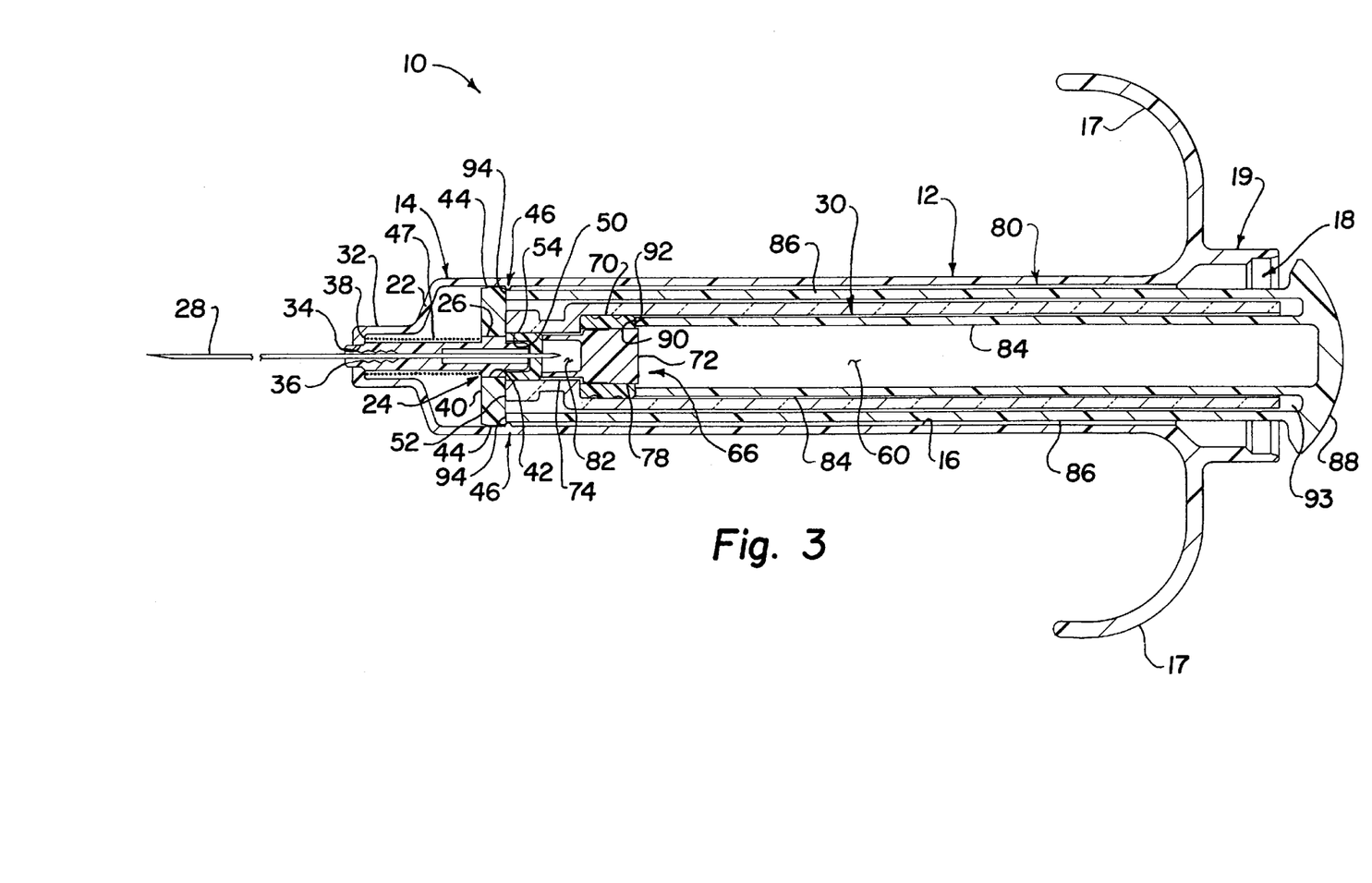
FIG. 3 is a cross sectional view along the center-line of the retractable medical device of FIG. 2 after the plunger has been depressed to expel substantially all fluid from the chamber of the carpule in the position that results at the end of an injection.

A retraction mechanism 20 is mounted in front portion 14 of housing 12. Seen better in FIG. 3, retraction mechanism 20 comprises elongated needle-holder body 22 with a widened part 24 having an outwardly facing surface 26 of limited length. Needle holder 22 circumscribes and holds a double-ended needle 28 which provides a fluid path into a carpule 30 to be described. Needle 28 may be a continuous needle as shown in FIG. 3 or fluidly connected separate portions having a forwardly and rearwardly extending portion to respectively engage tissue and engage a medicine supply in carpule 30. Front portion 14 of housing 12 includes a reduced diameter nose 32 having an opening 34 for front end 36 of needle holder 22. Front end 36 is a reduced diameter from body 22. It and the flange on nose 32 serve as a seat 38 for needle holder 22 in nose 32.

Needle holder 22 is held in place by means of push ring 40 having a central opening with an inwardly facing surface 42 which grippingly holds outwardly facing surface 26 of widened part 24. Push ring 40 has an outer rim or edge 44, here shown to be arcuate, preferably held in slidable, gripping contact with inner wall 16 of housing 12. An annular stop 46 comprising a slightly raised portion of inner surface 16 may be used to prevent rearward movement of the retraction mechanism.

It is preferable that stop 46 allow the slightly resilient edge of push ring 40 to be forced over it as the push ring slides forward during installation of retraction mechanism 20 from the back of the housing. It is also contemplated that stop 46 could be a larger stop that requires push ring 40 to be installed from the front of housing 12. In that case, housing 12 would be a two-part housing instead of a unitary housing as now shown in the drawings. It could have a detachable front part which is attached to the cylindrical housing after the retraction mechanism is installed. The stop could be individual inwardly radial protrusions or separated segments which prevent push ring 40 from moving in a retraction direction. A seat created by widened portion 24 receives the end of a biasing means in the form of compressed spring 47 which applies a retraction force against needle holder 22.

Figure 1:
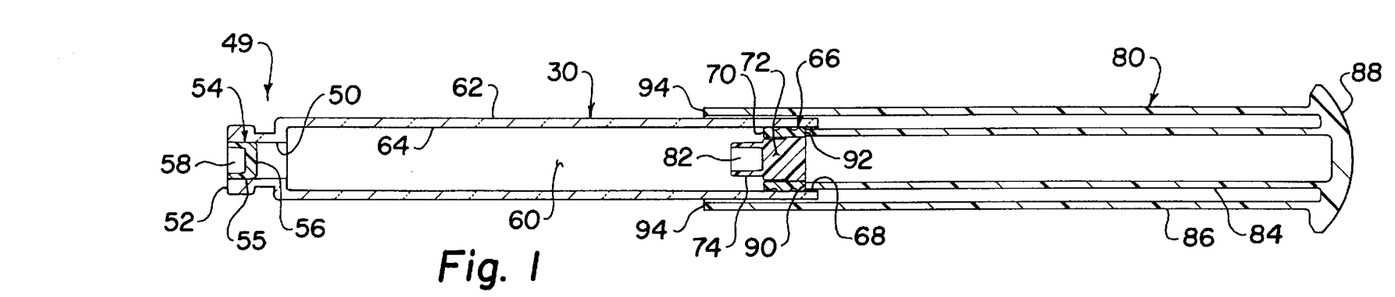
FIG. 1 is a longitudinal cross section through the center of the carpule and plunger in the initial assembled position.

Turning now to FIGS. 1, 2 and 2A, the outer edge 44 of push ring 40 is seen to be a relatively flat spot in the center with angled portions 48 on either side. The reduction in contacting surface area tends to increase the unit pressure at the interface between the push ring 40 and inner wall 16 and tends to compensate to some extent for manufacturing tolerance variations.

Figure 4:
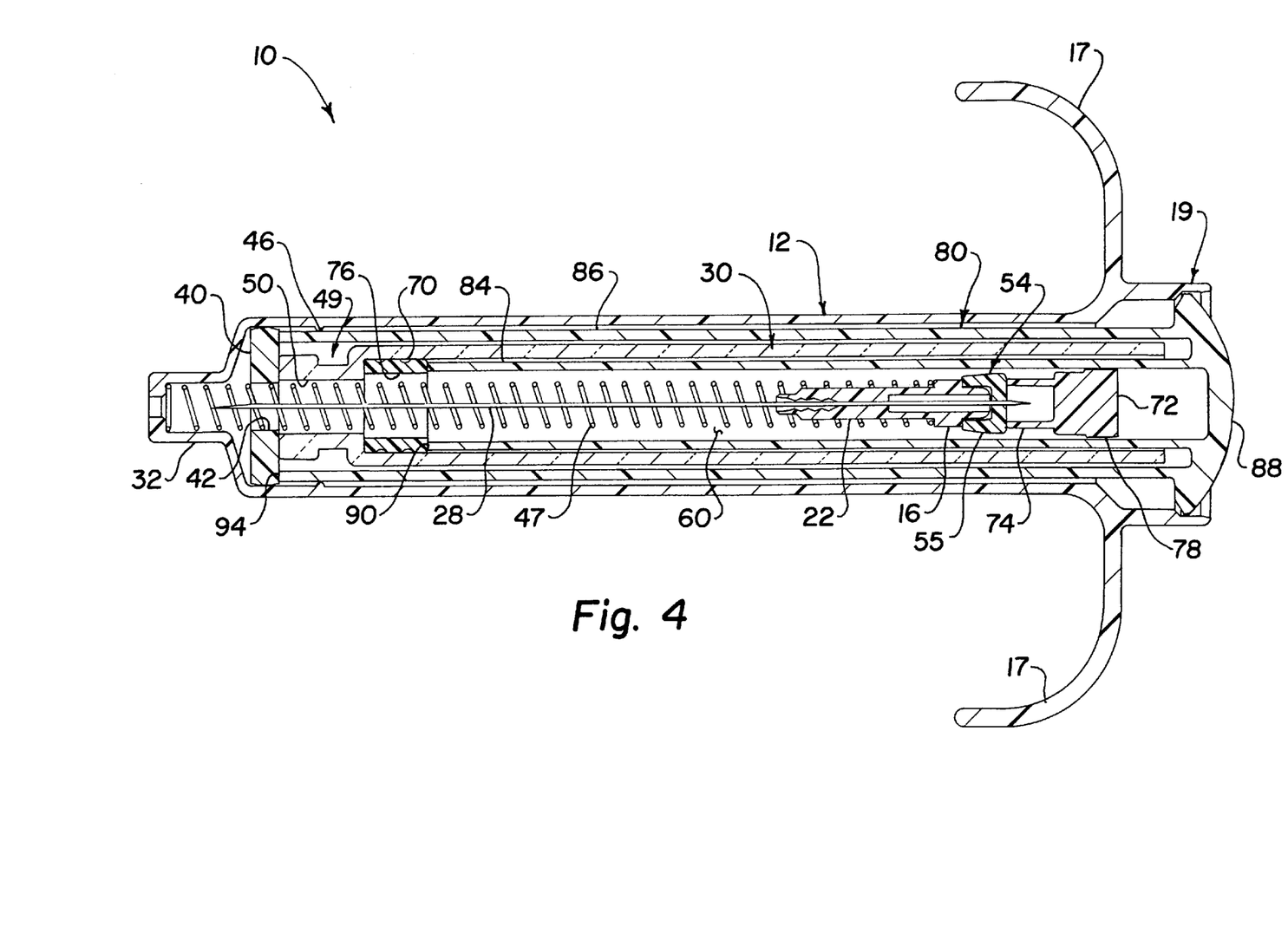
FIG. 4 represents the retractable medical device of FIG. 3 in a cross sectional view after the plunger has been depressed further from the fully injected position of FIG. 3 to show the fully retracted position of the needle-holding structure into the carpule.

Referring now to FIG. 1, carpule 30 has a reduced diameter front portion 49 having a relatively short opening 50 and a front surface 52. A slidable front seal 54 is lodged at the front of opening 50. Front seal 54 is a cup shaped member having a solid back 56, sides 55 in contact with the opening and an open side which serves as a socket 58. The side 55 may have an arcuate profile in its uncompressed state shown in FIG. 4. This may be configured to adjust the amount of sliding friction it takes to move seal 54 along the wall surface of opening 50.

A medicament chamber 60 is defined between the front portion 49, the elongated tubular wall 62 having an inner surface 64 and a slidable piston seal 66. The back of chamber 60 is defined by slidable two-part piston seal 66 lodged in opening 68 at the rear of carpule 30. Sliding piston seal 66 shown in FIG. 2B comprises outer rim member 70 and releasable core member 72 having a forwardly extending wall portion 74. Better seen in FIG. 2, rim member 70 is a cylindrical seal of suitable length having an opening comprising inwardly facing surface 76 therethrough. It is a sleeve which circumscribes releasable core member 72.

Core member 72 contacts inner surface 76 at land 78. Land 78 comprises a longitudinal surface which contacts rim 70 along a length which is less than the length of inwardly facing surface 76. Alternatively, the land could be a raised portion of rim member 70 and core member 72 could have a uniform cylindrical surface. The length of land 78 and the composition and fit of slidable core member 72 is selected so the two part piston seal will remain intact in the face of internal pressure generated in chamber 60 when a plunger 80 is depressed. The forwardly extending wall 74 of slidable core 72 is shown as cylindrical although it could be a plurality of individualized projections or legs which form a socket like opening 82. Socket 82 will receive the back end of needle 28. Wall portion 74 is adapted to fit inside opening 50, comprising the mouth of the carpule, and extend forwardly to contact front seal 54. This forward extension 74 of core member 72 allows the front seal member 54 and core member 72 to move together as a unit as retraction is being initiated. That way they are both in position to come free when needle holder 22 is released.

Returning now to FIGS. 1 and 2, plunger 80 has an inner wall 84 and an outer wall 86, parallel and spaced apart. These walls are preferably tubular for stability. Inner wall 84 and outer wall 86 may be connected at the back by a disappearing thumb cap 88 which will be closely received in widened part 19 of back opening 18 of housing 12. Inner wall 84 terminates in end surface 90 which is adapted to engage end surface 92 of rim member 70 seen in FIG. 2B. Inner wall 84 is adapted to closely enter opening 68 of the carpule with surface 90 in contact with surface 92 but not in contact with any portion of releasable core member 72.

Outer wall 86 is adapted to progressively receive carpule 30 while entering housing 12 as plunger 80 is depressed to move two-part piston seal 66 forward from the position of FIG. 2 to the end of injection position of FIG. 3. Outer wall 86 is closely received by inner wall 16 to provide some lateral stability to the assembled plunger and carpule as they are introduced. Outer wall 86 is preferably longer than inner wall 84 to partially engage the back end of the carpule in the manner shown in FIG. 1. This facilitates insertion of the carpule and plunger into the housing. End 94 of outer wall 86 stabilizes the combined carpule and plunger by virtue of sliding contact along wall surface 16.

More importantly, the relative length of the inner and outer walls 84, 86 of plunger 80 are such that piston seal 66 bottoms out in the front portion of carpule 30 at about the same time as circular end 94 reaches the outer edge portion of push ring 40 in preparation for retraction. Further depression of plunger 80 causes movement of carpule 30 as well as the plunger relative to the housing and allows outer wall 86 of the plunger and/or the front 52 of the carpule to remove push ring 40 from needle holder 22, which is grounded in the housing. The back end of needle holder 22 fits in socket 58 with the rear portion of needle 28 extending through seal 54. The back end of needle holder 22 may have a diameter smaller than socket 58 to control the amount of frictional engagement between side surface 55 and surface 50 or the combined diameter of the sides of socket 58 and back of needle holder 22 may be so designed. Socket 58 helps front seal member 54 remain on the back of needle holder 22 during retraction without getting crosswise or causing a jam and also helps align the carpule with the needle holder. When plunger 80 is depressed further beyond the end of injection position shown in FIG. 3, the plunger moves the push ring while substantially and simultaneously moving carpule 30 relative to the housing. Movement of the carpule beyond the end of injection position of FIG. 3 causes movement of rim member 70 relative to core member 72 and front seal 54 in preparation for retraction. Needle holder 22, front seal 54, and core member 72 are adapted to contact each other when plunger 80 is depressed sufficiently to bottom out piston seal 66 in carpule 30, a position which has expelled substantially all fluid from chamber 60 through needle holder 22.

Figure 5:
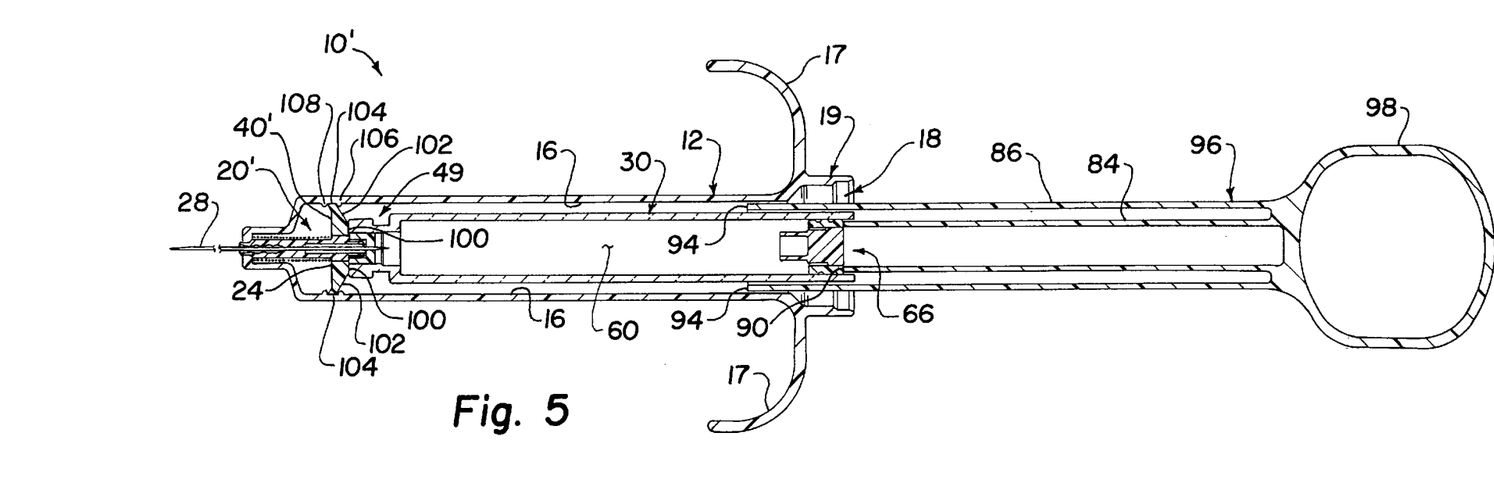
FIG. 5 represents a longitudinal cross sectional view through the center line of an alternative variation of the retractable medical device showing a forwardly angled dish shaped push ring with edges positioned between annular constrictions on the inner wall of the housing in the ready to inject position.

An alternate retractable medical device is designated retractable medical device 10' in FIGS. 5–10. Device 10' in FIG. 5 employs most of the same parts as the retractable medical device shown in FIGS. 1–4. Tubular housing 12 having an inner wall surface 16 is shown loaded with carpule 30 as before described. A modified plunger 96 differs from plunger 80 in that thumb cap 88 is replaced with thumb ring 98. This is more like the plunger dentists are used to but does not have the nonreusable feature of the syringe having the disappearing thumb cap. Plunger 96 has the same inner wall 84 and outer wall 86 as plunger 80 designed the same way to operate two-part sliding piston seal 66 to expel fluid from chamber 60. Structure 10' differs from structure 10, with the exception of the thumb ring, by an alteration to the retraction mechanism. Retraction mechanism 20' is otherwise identical to mechanism 20 except for the substitution of push ring 40' for push ring 40. Push ring 40' has a center body portion 100 which in FIG. 5 is shown slightly smaller in diameter than the diameter of front portion 49 of carpule 30. Push ring 40' has a forwardly angled outer rim portion 102 having an outer edge 104 in contact with inner wall surface 16.

Figure 8:
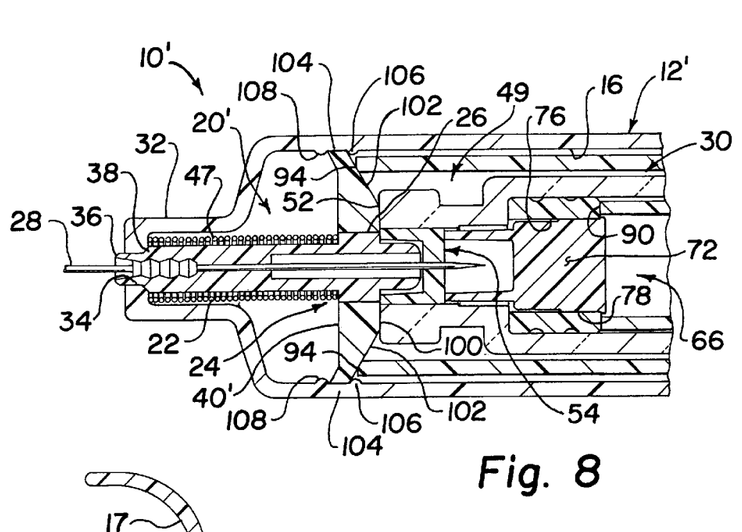
FIG. 8 is an enlarged cut away cross sectional view of the front portion of the medical device of FIG. 6 showing the plunger in a position to prevent deflection and jamming of the angled edges of the push ring against the stop structures formed on the inner wall of the housing.

Turning now to the enlarged view of FIG. 8, stop structure 106, 108 preferably comprises annular protrusions 106, 108 on inner surface 16 of housing 12'. Protrusions 106, 108 are the only difference between housing 12 and 12' whereby stop structures 106, 108 are placed above and below outer edge 104 of angled portions 102. When force is imposed on center portion 100 during an injection by front surface 52 of carpule 30, carpule 30 tends to jam the outer end 104 of outer rim portion 102 by slight flexing outwardly of alternate push ring 40'.

Figure 9:
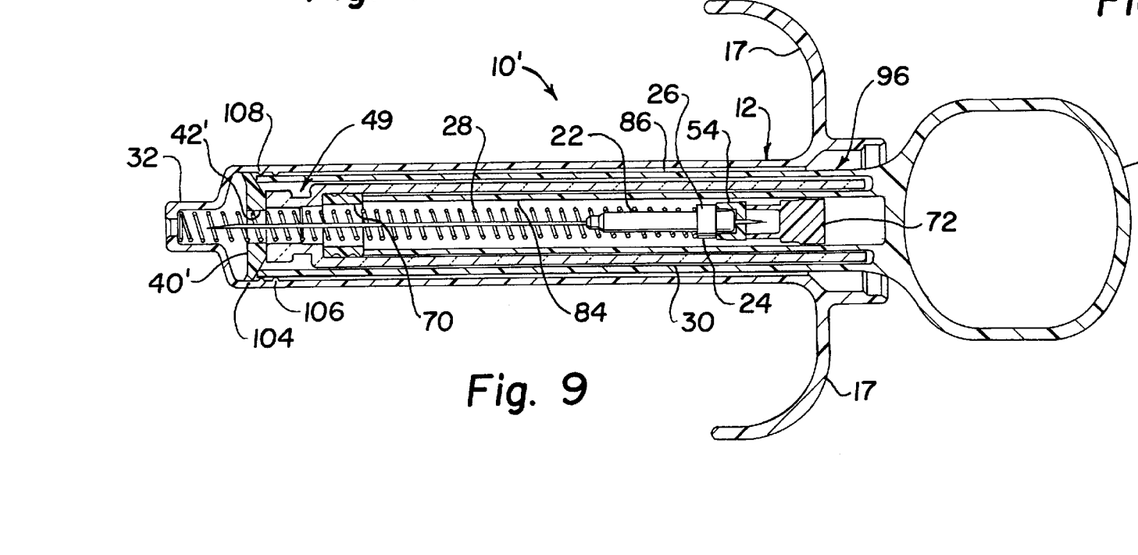
FIG. 9 is a cross sectional view of the retractable medical device of FIGS. 5, 6 and 8 after the plunger has been depressed beyond the position of FIG. 8 to cause relative movement of the push ring and carpule relative to the needle holder and create a passage for the retraction of the needle holder and needle shown in the fully retracted position.

At the end of the injection (the position of FIG. 8), further depression of modified plunger 96 pushes the outer rim portion of push ring 40' away from the stop structure so that push ring 40' can then be removed from widened part 24 of needle holder 22. This movement simultaneously causes motion of carpule 30 and rim member 72 relative to sliding front seal 54 and removable core portion 72 of two-part slidable piston seal 66. Modified plunger 96 and push ring 40' move forward while grounded needle holder 22 remains in place. The thickness and shape of push ring 40' is selected to function this way. A slight degree of flexibility through material or thickness variations is preferred to assure the jamming action occurs in response to force imposed by carpule 30 without removal of push ring 40'. FIG. 9 shows the result upon further depression of modified plunger 96 from the position of FIG. 8 where it can be seen that push ring 40' has been demounted by being moved forward by force imposed by the front portion of carpule 30 and outer wall 86. This has moved push ring 40' forward demounting it from widened part 24 of needle holder 22 and contemporaneously driven the stacked front seal and core member 72 rearwardly in the carpule where they are retained.

Figure 7:
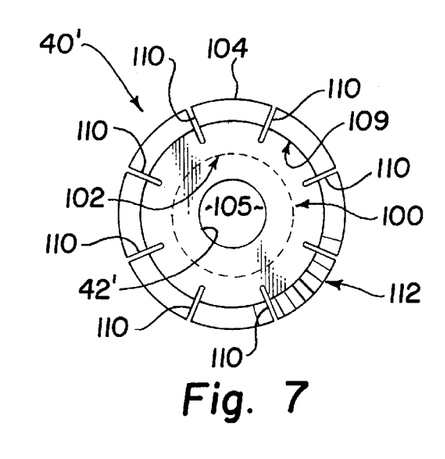
FIG. 7 illustrates an alternative design for the dish shaped push ring of FIGS. 5–9 showing forwardly angled segments comprising the angled outer rim of the alternate push ring which are more easily flexed to facilitate jamming of the push ring in opposition to forward movement.

FIG. 7 is a variation of push ring 40' of FIG. 8 showing extreme outer edge 104 and a central opening 105 with an inwardly facing surface 42'. Surface 42' slidingly grips surface 26 where it is held by needle holder 22 in opposition to compressed spring 47. This is preferably a frictional engagement. Center body portion 100 in FIG. 7 is represented by that portion between surface 42' and the dotted circle. The portion outwardly from the dotted circle is the forwardly angled outer rim portion 102 which may have additional change of direction 109. Flexibility of push ring 40' can be increased by adding a plurality of segmenting grooves 110, spaced evenly around the periphery, extending radially through most of angled portion 102. Additionally, a plurality of radial separations 112 may be added to increase flexibility of the outer edge.

In operation, the back end of carpule 30 is associated with the front of the plunger as shown in FIG. 1. Then the plunger and carpule assembly is introduced into open back end 18 of housing 12 and carpule 30 is moved forward until seal 54 is punctured by the rearwardly extending portion of needle 28 and some resistance is felt as the front of the carpule bottoms out against push ring 40. Socket 58 in sliding front seal 54 receives the back end of needle holder 22. The medical device is now in the initial position of FIG. 2 ready for use.

As needle 28 is inserted into a patient, plunger 80 is depressed to inject the contents of chamber 60 through needle 28. Push ring 40 grips the needle holder tightly enough to resist force imposed on the carpule by depression of the plunger. When the plunger is depressed to empty the carpule, two-part piston seal 66 comes to bottom against a reduced diameter back of front portion 49. This brings end 94 of outer wall 86 in contact with the outer edge portion of ring member 40. At this point, wall portion 74 of member 66 has entered opening 50 and is in contact with back wall 56 of sliding front seal 54. This position is referred to as the end of injection position which is shown in FIG. 3.

Further depression of the plunger will cause retraction of the needle from the patient in one quick motion with the needle being withdrawn into the housing and the retractable parts lodged in the carpule. As the plunger is depressed, inner wall 84 pushes against rim 70 which is bottomed in the front of the carpule. Simultaneously, outer wall 86 pushes against the outer edge portions of push ring 40 to begin sliding the push ring forward off needle holder 22. The combined action of the front of the carpule and the outer wall of the plunger slides the push ring forward along the interface 26, 42. At the same time, forward movement of front seal 54 and core member 72 is prevented by needle holder 22 which is grounded in the housing. Since rim member 70 is restrained by inner wall 84 which is moving forward with the carpule, the front seal member and core member can be seen as moving rearwardly as a unit relative to the carpule. When plunger 80 is moved forward enough to separate the push ring from the needle holder, the core member may be loose or nearly loose from the rim member. As push ring 40 frees the needle holder, the remaining pressure on thumb cap 88 instantly moves sliding seal 54 through opening 50 of front portion 49 of the carpule and spring 47 drives needle holder 22 and needle 28 through the opening of the mouth of the carpule into chamber 60 where they remain biased in the retraction direction. The edges of thumb cap 88 are closely received in widened opening 19 making it very difficult or impossible to remove the plunger or the now retracted components from housing 12.

It is evident the amount of movement necessary to remove push ring 40 may be altered by changing the length of the interfacing surfaces 26, 42 on the needle holder and push ring respectively. Although the push ring is preferably held on the widened part of the needle holder by friction along the interfaces 26, 42, it is also possible to employ an adhesive there which will break away under a predetermined force. Core member 72 is preferably frictionally engaged with rim member 70. The diameter of the mouth of the carpule and the core member must, of course, be large enough to allow the widened part of the needle holder and the sliding front seal the pass therethrough. Core member 72 must be held tightly enough within rim member 70 to withstand the pressure generated force imposed as the plunger is depressed during an injection.

Figure 6:
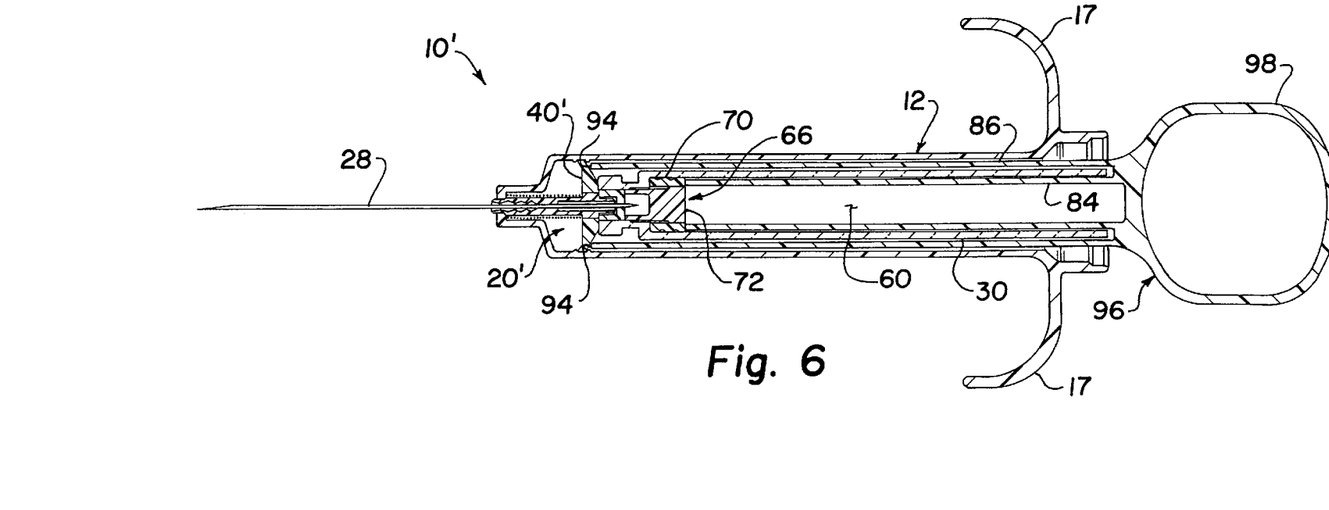
FIG. 6 shows the retractable medical device of FIG. 5 after the plunger has been depressed to a first position where substantially all fluid is dispensed from the carpule and part of the plunger has reached the outer edge of the push ring where further depression of the plunger will trigger retraction.

The alternate embodiment of FIGS. 5–9 functions in a similar manner, the difference being an alteration of the push ring 40' and the provision of a stop structure 106, 108 which captures the edge 104 of push ring 40'. When force is imposed on the center portion by carpule 30, the dish shaped push ring tends to expand outwardly and bind more tightly against surface 16, including some binding effect on the widened part of needle holder 22. FIG. 5 shows the ready to inject position and FIG. 6 shows the end of injection position, comparable to FIGS. 2 and 3.

In FIG. 6, once end 94 of tubular wall 86 pushes against the outer edge portion of push ring 40', it releases edge portion 104 by relieving the binding condition. It can be configured to contact push ring 40' just before the piston seal bottoms out in the front of carpule 30 to facilitate releasing the edge of the push ring from the stop structure. As the edges of push ring 40' are released from the stop structure, the plunger and carpule move forward to remove the push ring from the needle holder and simultaneously slide the carpule forward with respect to the sliding front seal and core member 72 to reach the retracted position of FIG. 9 as before described. Like the previous embodiment, the embodiment of FIGS. 5–9 is intended as a single use product. Although the thumb ring of the alternate design makes it possible to remove the plunger after retraction, the parts are so disassembled as to be extremely difficult of reassembly. In particular, rim member 70 is stuck in the bottom of the carpule with no perceptible way to dislodge it.

In the best mode, the carpule is glass and the housing and plunger are conventional syringe plastics. The sliding front seal and rim member are preferably rubber of a medical grade having long shelf life without interacting with medication. Likewise, the core member is glass or a hard plastic which will not react with desired medications. The push ring and needle holder are preferably polypropylene selected to be semi-rigid with a limited amount of flexibility for use in the alternate embodiment.

Although the invention has been disclosed above with regard to a particular and preferred embodiment, which is advanced for illustrative purposes only, it is not intended to limit the scope of this invention. It will be appreciated that various modifications, alternatives, variations, etc., may be made without departing from the spirit and scope of the invention as defined in the appended claims.

I claim:

1. A retractable medical device for dispensing fluid from a carpule, comprising:
    a tubular housing having a front portion, an inner wall surface and an open back end;
    a carpule to fit in the housing, the carpule having a front with an opening having a slidable front seal and a wall extending rearwardly with an opening in back having sliding two part piston seal with a releasable core member;
    a plunger having an outer wall and an inner wall wherein said outer wall is adapted to progressively receive the carpule while entering the housing and said inner wall is adapted to move the piston seal forward to the front of the carpule;
    a retraction mechanism mounted in the front portion of the housing comprising a needle holder body with a widened part and a separable member grippingly holding the widened part of the needle holder and being restrained by the inner wall surface of the housing, the needle holder including the needle portion extending forwardly and rearwardly from the needle holder body and biasing means applying a retraction force to the needle holder;
    the carpule being installable in the housing with the front opening facing the separable member and the front seal being punctured by the rearwardly extending needle portion; and
    retraction being triggered by depression of the plunger to cause relative movement of the separable member and carpule relative to the needle holder whereby a passage for retraction of the needle holder is opened into the carpule upon removal of the separable member to free the needle holder for retraction into the carpule in response to the retraction force.

2. The medical device of claim 1 wherein the two part sliding piston seal comprises a rim member of a suitable length circumscribing the releasable core member wherein the rim member and core member contact each other along a longitudinal distance which is less than said length.

3. The medical device of claim 2 wherein the outer wall of the plunger extends forwardly beyond the plunger inner wall to partially receive the back of the carpule and help position it in the housing.

4. The medical device of claim 1 wherein the plunger is depressed to empty the carpule, the relative length of the inner and outer wall of the plunger is such that the piston seal bottoms out in the carpule at about the same time as the outer wall of the plunger reaches the separable member thereby causing movement of the carpule as well as the plunger relative to the housing during further depression of the plunger to remove the separable member from the needle holder.

5. The medical device of claim 4 wherein the needle holder, front seal and core member are adapted to contact each other when the plunger is depressed to bottom out the piston seal in the carpule so that further depression of the plunger to remove the separable member moves the carpule and separable member relative to the front seal and core member, in preparation for retraction.

6. The medical device of claim 1 wherein the inner wall surface of the housing has a small stop structure positioned under the separable member, said structure being adapted to provide overcomable resistance to movement of the separable member.

7. The medical device of claim 6 wherein the separable member has a center body portion and a forwardly angled outer rim positioned behind the stop structure whereby force imposed on the separable member by the carpule during an injection tends to jam the outer rim against the housing without removing the separable member until the outer wall of the plunger releases the outer rim of the separable member from the stop structure.

8. The medical device of claim 7 wherein the angled outer rim comprises a plurality of forwardly angled segments that interact with the stop structure on the inner wall surface of the housing to hold the separable member in place until it is released by the plunger.

9. The medical device of claim 6 wherein the plunger is depressed to empty the carpule, the relative length of the inner and outer wall of the plunger is such that the piston seal bottoms out in the carpule at about the same time as the outer wall of the plunger reaches the separable member thereby causing movement of the carpule as well as the plunger relative to the housing during further depression of the plunger to remove the separable member from the needle holder.

10. The medical device of claim 9 wherein the needle holder, front seal and core member are adapted to contact each other when the plunger is depressed to bottom out the piston seal in the carpule so that further depression of the plunger to remove the separable member moves the carpule and separable member relative to the front seal and core member, in preparation for retraction.

11. The medical device of claim 10 wherein the two part sliding piston seal comprises a rim member of a suitable length circumscribing the releasable core member wherein the rim member and core member contact each other along a longitudinal distance which is less than said length.

12. The medical device of claim 1 wherein the needle holder has a projection and the front of the carpule has a socket to receive said projection when the carpule is inserted in the housing thereby facilitating alignment of the carpule and needle holder.

13. The medical device of claim 12 wherein the front seal is a cup shaped member with an open side that serves as said socket.

14. A retractable medical device for dispensing fluid from a carpule, comprising:
- a tubular housing having a wall defining a front end portion, a main body portion and an open back end, the wall having an inner surface defining a hollow interior;
- a retraction mechanism mounted in the front end portion of the housing, comprising:
  - a needle holder having an elongated body with a front, a back and a widened part of the body spaced behind the front
  - needle portions extending from the front and back of the needle holder
  - a spring mounted under the widened part of the needle holder body to apply a retraction force thereto,
  - a releasable member grippingly mounted around the widened part of the needle holder and extending outwardly in sliding gripping contact with the inner wall of the housing to hold the needle holder in place against the retraction force provided by the spring;
- a carpule for fluid to be dispensed, the carpule having a front end with an opening and slidable puncturable front seal, a body comprising a wall extending rearwardly and an opening in back with a two part slidable piston seal, the carpule being adapted to slide into the housing whereby the front seal is punctured by the needle;
- a plunger adapted to progressively receive the carpule while entering the housing and pressing the slidable piston forward to dispense fluid through the needle until depression of the plunger reaches an end of injection position wherein substantially all fluid is dispensed and part of the plunger reaches the releasable member; and
- the plunger being further depressible along with said carpule beyond the end of injection position to trigger retraction by moving the releasable member from the widened part of the needle holder while dislodging the front seal and part of the piston seal whereby the retraction force drives the needle holder and needle through the front opening into the carpule where they are safe.

15. The medical device of claim 14 wherein the inner wall surface of the housing has a small stop structure positioned under the releasable member, said structure being adapted to provide overcomable resistance to movement of the releasable member.

16. The medical device of claim 15 wherein the releasable member has a center body portion and a forwardly angled outer rim positioned behind the stop structure whereby force imposed on the releasable member by the carpule during an injection tends to jam the outer rim against the housing without removing the releasable member until the outer wall of the plunger releases the outer rim of the releasable member from the stop structure.

17. The medical device of claim 16 wherein the angled outer rim comprises a plurality of forwardly angled segments that interact with the stop structure on the inner wall surface of the housing to hold the releasable member in place until it is released by the plunger.

18. A carpule for a retractable medical device comprising:
- a cylindrical wall defining a fluid chamber, said wall having a front end with an opening into the fluid chamber and an open back end;
- a slidable front seal lodged in the opening of the front end;
- a sliding piston seal lodged in the open back end wherein the piston seal has an outer rim portion in sliding sealing contact with the wall of the fluid chamber and a forcibly removable core;
- wherein the sliding piston seal can be driven forward to displace fluid from the fluid chamber when a fluid path is provided by a needle portion traversing the front seal;
- the sliding piston seal having a position at the front of the fluid chamber that corresponds to the end of injection position whereby substantially all fluid has been dispensed from the fluid chamber; and
- the front seal and forcibly removable core of the sliding plunger seal can be driven back into the fluid chamber to clear the way for retractable parts to enter the fluid chamber through said opening.

19. The carpule of claim 18 wherein the inner surface of the outer rim portion and the outer surface of the forcibly removable core are in contact over only a portion of their extent to reduce the amount of movement required to disengage the core from the rim.

20. The carpule of claim 18 wherein the removable core part of the piston seal and the slidable front seal are configured to come together at the end of injection position so they can be moved together.

21. The carpule of claim 20 wherein the inner surface of the outer rim portion and the outer surface of the forcibly removable core are in contact over only a portion of their extent to reduce the amount of movement required to disengage the core from the rim.

22. The carpule of claim 20 wherein the front of the carpule is shaped like a socket to receive the end of a needle holder.

23. The carpule of claim 22 wherein the front seal is a cup shaped member with an open side which serves as said socket.

24. The carpule of claim 23 wherein the inner surface of the outer rim portion and the outer surface of the forcibly removable core are in contact over only a portion of their extent to reduce the amount of movement required to disengage the core from the rim.

25. In a retractable medical device having a tubular housing having an inner wall surface and an open back end, a retraction mechanism mounted in the front of the housing, the retraction mechanism including a spring loaded needle holder and double ended needle, a carpule designed to fit in the housing, the carpule having a front end with sealed front opening which is punctured by the needle and a back end having a piston plug which is moved by a plunger which pushes the piston forward to empty the contents of the carpule through the double ended needle, the improvement comprising:
- the carpule has a slidable front seal in the front opening and a slidably removable core member in the center of the piston plug, wherein the slidable core member is brought adjacent to the front seal in response to depression of the plunger to expel substantially all the contents of the carpule;
- an opening for the needle holder to retract into the carpule is created by sliding removal of the slidable front seal from the front opening and sliding removal of the slidable core member from the piston;

the needle holder is positioned and held with the needle extended by means of a removable push ring circumscribing the needle holder, wherein the push ring is in forcible movable contact with a portion of the inner wall surface of the housing; and depression of the plunger after empty the contents of the carpule through the needle causes relative movement of the carpule and push ring relative to the needle holder thereby opening a passage into the carpule for retraction of the needle holder as it is being released by removal of the push ring.

26. The improvement of claim 25 wherein the front end of the carpule is supported against forward movement by the needle holder and/or push ring in response to depression of the plunger while an injection is being given.

27. The improvement of claim 26 wherein there is a wall of material which extends between the front seal and the core member when the piston has moved forward to expel the contents of the carpule.

28. The improvement of claim 27 wherein a portion of the core member extends into the front opening of the carpule when the carpule has been emptied by depression of the plunger.

29. The improvement of claim 28 wherein the carpule has a body portion in which the piston operates, said body portion having a larger inner diameter than the diameter of the front opening whereby a lateral stop surface is created at the back of said opening which provides a stop for the piston at the bottom of its forward travel.

30. A retractable medical device for dispensing fluid from a carpule, comprising:

a tubular housing with a longitudinally extending wall having an inner wall surface and an open back end;

a retraction mechanism mounted in the front of the housing, the retraction mechanism comprising a needle holder grounded in the housing, the needle holder having an elongate body, a widened portion and a demountable member grippingly mounted on the widened portion of the needle holder, the member having an outer portion slidingly gripping the inner wall of the housing in opposition to a biasing element applying a retraction force to the needle holder, the needle holder including forwardly and rearwardly extending needle portions with a fluid passage therethrough;

a removable carpule having an elongate wall comprising an opening in front sized to pass the needle holder and an opening in back, the carpule having a seal slidably lodged in the front opening and a piston seal slidably lodged in the back opening, the interior of the carpule defining a fluid chamber;

the carpule being installable into the housing behind the demountable member with the rearwardly extending needle portion extending through the front seal in fluid communication with the chamber;

the piston seal including an outer rim portion and a forcibly removable core, the piston seal being movable in sliding contact with the elongate wall of the carpule to a front position in the carpule to dispense substantially all fluid from the chamber;

a plunger having an inner wall adapted to move the piston seal to the front position in the carpule by pushing on the outer rim of the piston seal;

wherein further depression of the plunger moves the demountable member forward to demount it from the needle holder while freeing the front seal from its opening and freeing the core of the piston seal from the outer rim whereby the biasing element can drive the needle holder into the chamber thereby retracting the needle.

31. A retractable medical device for dispensing fluid from a carpule comprising:

a tubular housing having a front portion, an inner wall surface and an open back end;

a retraction mechanism mounted in the front portion of the housing comprising a needle holder including needle portions extending forwardly and rearwardly from the needle holder, a biasing element applying a retraction force to the needle holder and a separable member which cooperates with the inner wall surface of the housing to hold the needle holder and needle in a position for use;

a carpule to fit in the housing having a front opening sealed with a slidable front seal and a medicament chamber behind;

whereby the separable member is released from the needle holder and at least part of the needle enters the medicament chamber in response to depression of the plunger thereby safely retracting the needle.

32. In a retractable medical device having a tubular housing having an inner wall surface and an open back end, a retraction mechanism mounted in the front of the housing, the retraction mechanism including a retractable spring loaded needle holder and double ended needle, a carpule designed to fit in the housing, the carpule having a front end with sealed front opening which is punctured by the needle and a back end having a piston plug which is moved by a plunger which pushes the piston forward to empty the contents of the carpule through the double ended needle, the improvement comprising:

the carpule has a seal in front and a removable core member in the center of the piston, wherein the core member comes adjacent to the seal in response to depression of the plunger to expel the contents of the carpule;

removal of the seal from the front opening and the core member from the piston leaves an opening for the needle holder to retract into the carpule;

the needle holder is positioned and held with the needle extended by means of a separable member circumscribing the needle holder, which is restrained by the inner wall surface of the housing; and depression of the plunger to empty the contents of the carpule releases the needle holder by removal of the separable member from the needle holder whereby the needle holder and the needle enter the carpule through said front opening.

33. In a retractable medical device having a tubular housing having an inner wall surface and an open back end, a retraction mechanism comprising a spring loaded needle holder and double ended needle mounted in the front portion of the housing, a carpule designed to fit in the housing, the carpule having a front end with a front opening having a seal which is punctured by the needle and a back end having a piston plug which is moved by the plunger during an injection, the interior of the carpule behind the front opening comprising a chamber for fluid contents, whereby the piston is pushed forward to empty the contents of the carpule through the double ended needle, the improvement comprising:

releasable structure extending between the needle holder and the housing releasably holding the retraction mechanism in the housing;

the carpule has a slidable front seal in the front opening, a chamber behind the front opening and a removable core member in the piston plug;

depression of the plunger after emptying the contents of the carpule through the needle is accompanied by release of the releasable structure, sliding removal of the front seal from the front opening of the carpule and release of said core member from the piston plug to create an opening for the needle holder into said chamber of the carpule, caused by depression of the plunger;

whereby the needle holder is automatically retracted into the carpule by depressing the plunger after the carpule is emptied.

34. The improvement of claim 33 wherein the plunger has an outer wall that progressively receives the carpule and an inner wall which progressively pushes the piston plug forward within the carpule as the plunger is depressed.

35. The improvement of claim 34 wherein the releasable structure for holding the retraction mechanism in the housing is released in response to forward movement of the carpule relative to the tubular housing caused by depression of the plunger after the carpule is emptied.

36. The improvement of claim 35 wherein the needle holder serves as a stop for the slidable front seal as the carpule moves forward thereby removing the front seal of the carpule to create an opening for entry of the needle holder.

37. The improvement of claim 1 wherein the removable core member and front seal move together after the carpule is emptied by depression of the plunger.

38. The improvement of claim 37 wherein an extension of the removable core member or the front seal causes contact between them to cause them to move together.

39. A retractable medical device for dispensing fluid from a carpule, comprising:

a tubular housing having a front end portion and a retractable needle for dispensing the fluid contents of a carpule;

a sealed carpule having a fluid chamber in fluid communication with the retractable needle;

a depressible plunger which at the end of an injection can be depressed further causing the retractable needle to automatically enter the fluid chamber.

* * * * *

UNITED STATES PATENT AND TRADEMARK OFFICE
CERTIFICATE OF CORRECTION

PATENT NO : 5,997,512
DATED : December 7, 1999
INVENTOR(S) : Thomas J. Shaw

It is certified that error appears in the above-identified patent and that said Letters Patent is hereby corrected as shown below:

Col. 9, line 44
  replace "opening in back having sliding"
  with --opening in back having a sliding--.

Signed and Sealed this

Sixth Day of March, 2001

Attest:

NICHOLAS P. GODICI

Attesting Officer    Acting Director of the United States Patent and Trademark Office